(12) United States Patent
Ohta et al.

(10) Patent No.: US 9,084,695 B2
(45) Date of Patent: Jul. 21, 2015

(54) PRESSURE-SENSITIVE ADHESIVE TAPE PACKAGE

(75) Inventors: Shigeo Ohta, Tokyo (JP); Nobuo Tsutsumi, Tokyo (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 699 days.

(21) Appl. No.: 13/140,895

(22) PCT Filed: Dec. 18, 2009

(86) PCT No.: PCT/JP2009/071144
§ 371 (c)(1),
(2), (4) Date: Jun. 29, 2011

(87) PCT Pub. No.: WO2010/073993
PCT Pub. Date: Jul. 1, 2010

(65) Prior Publication Data
US 2011/0253304 A1    Oct. 20, 2011

(30) Foreign Application Priority Data

Dec. 25, 2008 (JP) ................................ P2008-331465
Jan. 30, 2009 (JP) ................................ P2009-020038
Sep. 18, 2009 (JP) ................................ P2009-217780

(51) Int. Cl.
*B29C 65/00* (2006.01)
*B32B 37/26* (2006.01)
(Continued)

(52) U.S. Cl.
CPC ........... *A61F 15/001* (2013.01); *A61F 13/0008* (2013.01); *A61F 13/00085* (2013.01);
(Continued)

(58) Field of Classification Search
CPC .............. A61F 13/0008; A61F 15/001; A61F 13/00085; A61F 13/023; A61F 2013/00817; A61F 13/02; A61F 13/0203; A61F 2013/00897; A61K 9/7084; B32B 37/26; B32B 27/00; B29C 65/18; B29C 65/02; B29C 66/004
USPC ........ 156/289, 73.5, 304.5, 308.6; 602/42, 57
See application file for complete search history.

(56) References Cited

U.S. PATENT DOCUMENTS 2,721,550 A    10/1955  Banff
2,969,144 A     1/1961  Zackheim
(Continued)

FOREIGN PATENT DOCUMENTS

AU    17814/83    *  2/1984
EP    0 101 298 A2   2/1984
(Continued)

OTHER PUBLICATIONS

English translation of JP1095728; Apr. 14, 1998, Goto et al.*
(Continued)

*Primary Examiner* — Sonya Mazumdar
(74) *Attorney, Agent, or Firm* — Nath, Goldberg & Meyer; Joshua B. Goldberg

(57) ABSTRACT

A pressure-sensitive adhesive tape package is provided. The pressure-sensitive adhesive tape package accommodates an adhesive tape having a support and an adhesive agent layer provided on one surface of the support, the adhesive tape being bent into a first portion and a second portion such that the adhesive agent layer faces outward. Moreover, the pressure-sensitive adhesive tape package can include a first release sheet releasably attached to the adhesive agent layer of the first portion of the adhesive tape, and a second release sheet releasably attached to the adhesive agent layer of the second portion of the adhesive tape to seal the adhesive tape with the first release sheet between the first and second release sheets. In this configuration, the conventionally existing package can be eliminated. Moreover, when the second release sheet is removed from the adhesive agent layer of the second portion of the adhesive tape, half of the adhesive agent layer is exposed.

14 Claims, 13 Drawing Sheets

(51) Int. Cl.
*B32B 27/00* (2006.01)
*A61F 13/00* (2006.01)
*A61K 9/70* (2006.01)
*B32B 27/26* (2006.01)
*A61F 15/00* (2006.01)
*B29C 65/06* (2006.01)

(52) U.S. Cl.
CPC ............ *A61K9/7084* (2013.01); *B29C 66/004* (2013.01); *B32B 27/26* (2013.01); *B29C 65/06* (2013.01); *B29C 66/43* (2013.01)

(56) References Cited

U.S. PATENT DOCUMENTS

| | | | |
|---|---|---|---|
| 2,969,145 A | | 1/1961 | Hannauer, Jr. |
| 3,018,881 A * | | 1/1962 | Wall ........................... 206/441 |
| 3,457,919 A | | 7/1969 | Harbard |
| 4,264,008 A | | 4/1981 | Kozlow |
| 4,265,234 A | | 5/1981 | Schaar |
| 4,304,333 A | | 12/1981 | Kozlow, Sr. |
| 4,587,146 A | | 5/1986 | Anhäuser et al. |
| 4,638,043 A | | 1/1987 | Szycher et al. |
| 5,052,381 A | | 10/1991 | Gilbert et al. |
| 5,266,371 A | | 11/1993 | Sugii et al. |
| 5,275,284 A | | 1/1994 | Onotsky |
| 5,397,297 A | | 3/1995 | Hunter |
| 5,840,052 A | | 11/1998 | Johns |
| 5,998,694 A | | 12/1999 | Jensen et al. |
| 6,120,637 A * | | 9/2000 | Barry ........................... 156/252 |
| 6,124,522 A * | | 9/2000 | Schroeder ..................... 602/57 |
| 6,140,549 A | | 10/2000 | Pompei, Jr. |
| D477,086 S | | 7/2003 | Tsuruda et al. |
| 6,953,602 B2 | | 10/2005 | Carte et al. |
| D512,509 S | | 12/2005 | Yamasoto et al. |
| D537,947 S | | 3/2007 | Miyachika et al. |
| D545,441 S | | 6/2007 | Miyachika et al. |
| D668,766 S | | 10/2012 | Miyachi et al. |
| D670,395 S | | 11/2012 | Wakamatsu et al. |
| D678,534 S | | 3/2013 | Durand et al. |
| 8,674,166 B2 * | | 3/2014 | Hansen ........................ 602/54 |
| 2004/0004014 A1 | | 1/2004 | Grossman |
| 2005/0075595 A1* | | 4/2005 | Hill ............................... 602/41 |

FOREIGN PATENT DOCUMENTS

| | | | |
|---|---|---|---|
| GB | 883916 | | 12/1961 |
| GB | 2019036 A | * | 10/1979 |
| JP | 50-133797 | | 11/1975 |
| JP | 59-49762 A | | 3/1984 |
| JP | 5949762 A | * | 3/1984 |
| JP | H1095728 A | | 4/1998 |
| JP | 2003-190206 A | | 7/2003 |
| JP | 2003190206 A | * | 7/2003 |
| JP | 2003-325575 A | | 11/2003 |
| JP | 2003325575 A | * | 11/2003 |
| JP | 2004-24752 A | | 1/2004 |
| JP | 2004081558 A | | 3/2004 |
| JP | 3689807 B2 | | 6/2005 |
| JP | 3689807 B2 | * | 8/2005 |
| JP | 2007-75601 A | | 3/2007 |
| JP | 2007-75602 A | | 3/2007 |
| JP | 2007075601 A | * | 3/2007 |
| JP | D1398441 S | | 10/2010 |
| JP | D1398441 S | * | 10/2010 |
| JP | D1403401 S | | 12/2010 |
| JP | D1403401 S | * | 12/2010 |
| JP | 5571232 B2 | | 8/2014 |
| JP | 5635911 B2 | | 12/2014 |
| KR | D3001360890000 S | | 1/1993 |
| TW | D138261 S | | 12/2010 |
| WO | 01/35884 A1 | | 5/2001 |
| WO | 2010071104 A1 | | 6/2010 |
| WO | WO 2010073993 A1 | * | 7/2010 |

OTHER PUBLICATIONS

English translation of JP2004-081558; Mar. 18, 2004, Ito et al.*
International Preliminary Report on Patentability, International Application No. PCT/JP2009/070820, dated Jul. 5, 2011, seven (7) pages.
International Search Report for PCT Application No. PCT/JP2009/071144; search completed on Mar. 4, 2010; search mailed on Mar. 16, 2010; four pages total.
Notice of Allowance and Fees Due for U.S. Appl. No. 13/139,438 dated Aug. 27, 2013, 23 pages.
Chinese Office Action, CN Patent Application No. 200980150447.4, dated Dec. 21, 2012, five (5) pages.
Notice of Allowance issued by the U.S. Patent and Trademark Office for U.S. Appl. No. 29/404,447; mailed on May 10, 2013.
An Office Action issued for Singapore Patent Application No. 201104340-3 on Jan. 28, 2013.
European Patent Office Search Report, issued on Mar. 15, 2013, in related European Patent application 09834794.1, six (6) pages.
An Office Action issued for U.S. Appl. No. 13/139,438 on Mar. 26, 2013.
Search Report for Singapore Patent Application No. 2011043395 mailed on Jun. 28, 2013.
International Preliminary Report on Patentability, issued Aug. 9, 2011, for the corresponding PCT International Application No. PCT/JP2009/071144, nine (9) pages.
Notice of Allowance for U.S. Appl. No. 29/404,447 dated Aug. 20, 2013, 10 pages.
Examination Report issued on Aug. 8, 2012 for New Zealand Patent Application No. 593967.
Japanese Patent Application No. P2010-544040, Notice of Allowance dated Dec. 16, 2014, three (3) pages.

* cited by examiner

Fig.3
(a)
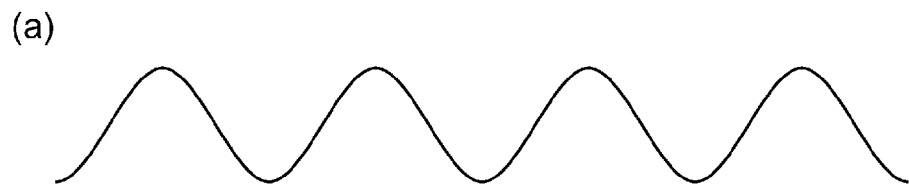
(b)
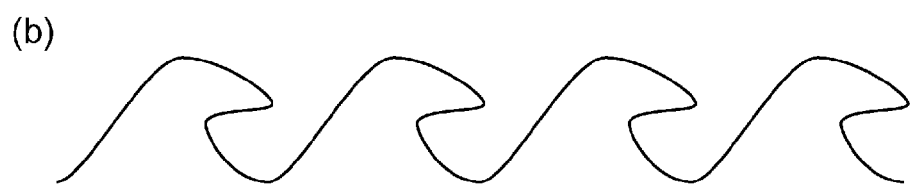
(c)
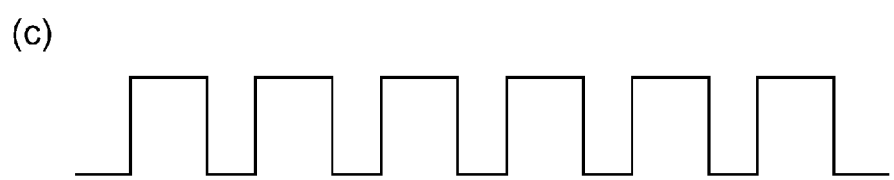
(d)

Fig.4
(a)
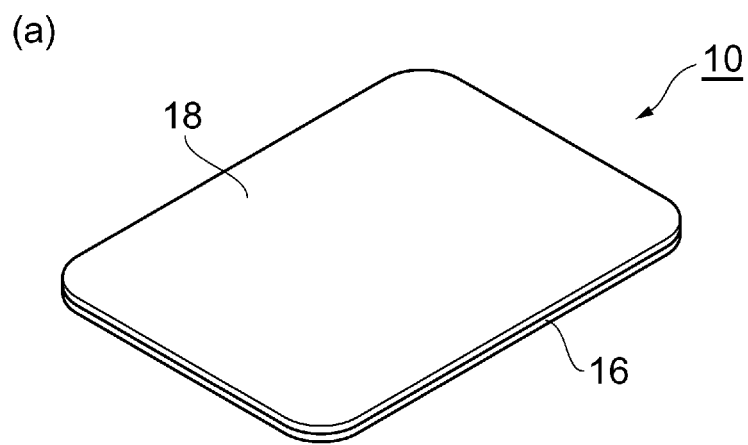
(b)
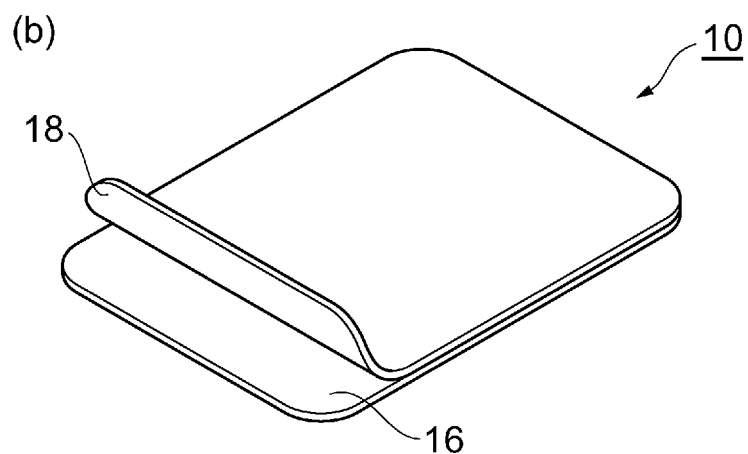
(c)
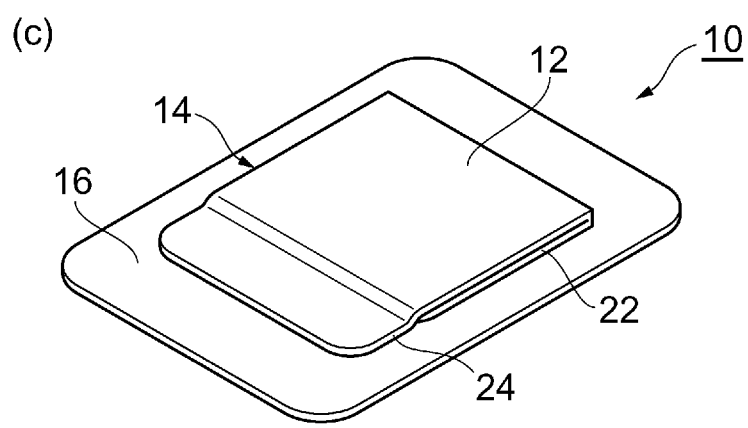

Fig.8
(a)
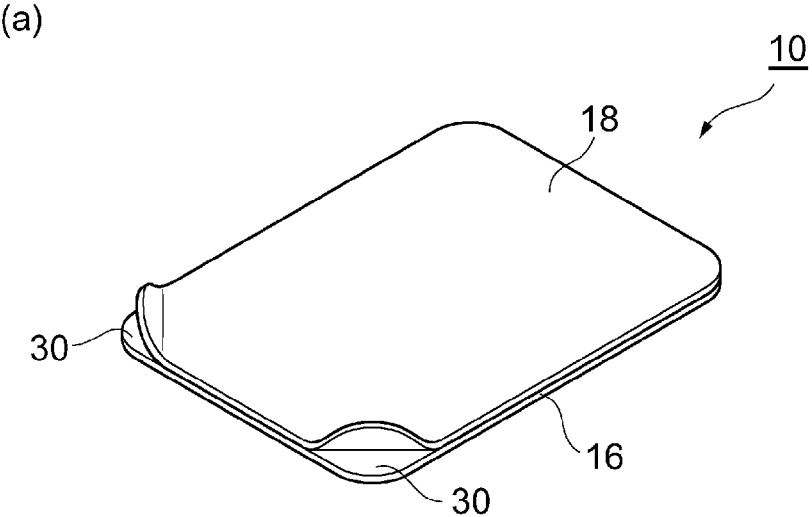
(b)
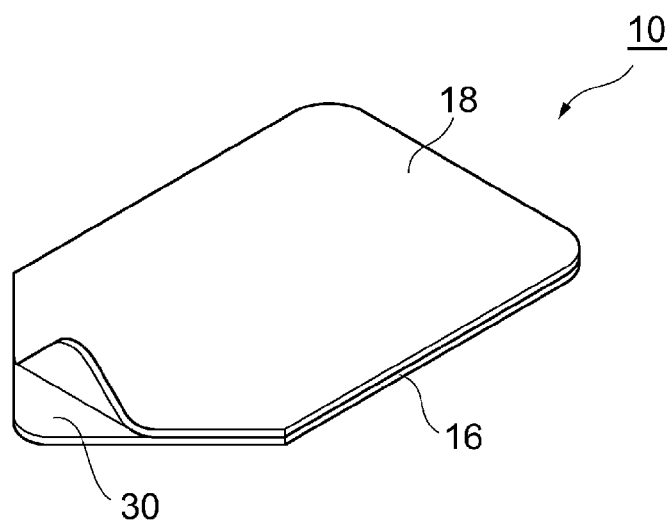

Fig.11
(a)
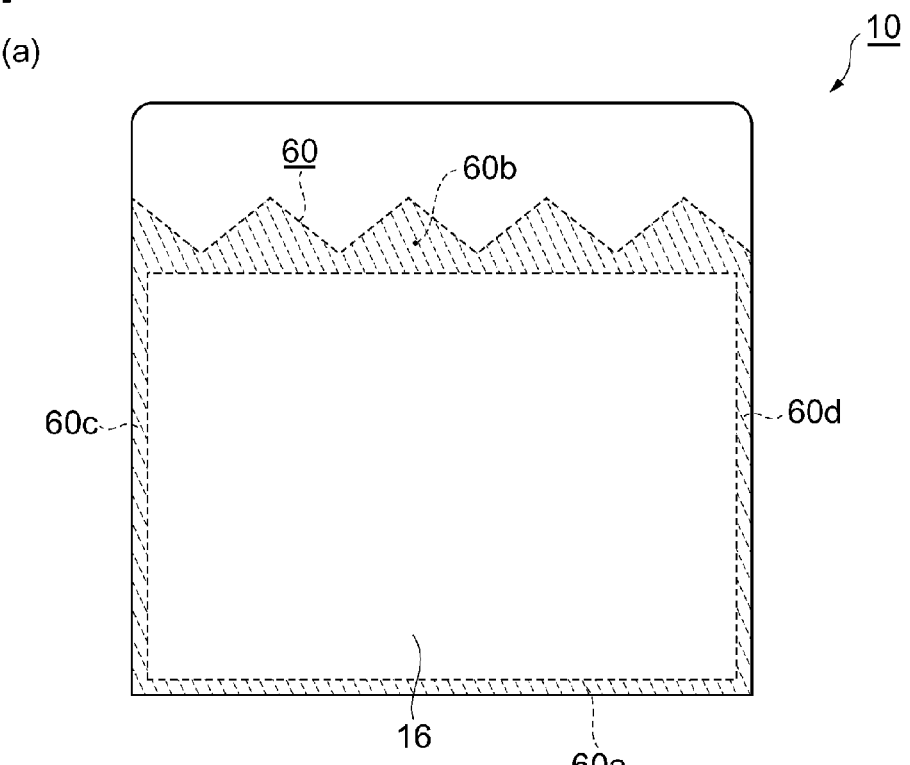
(b)
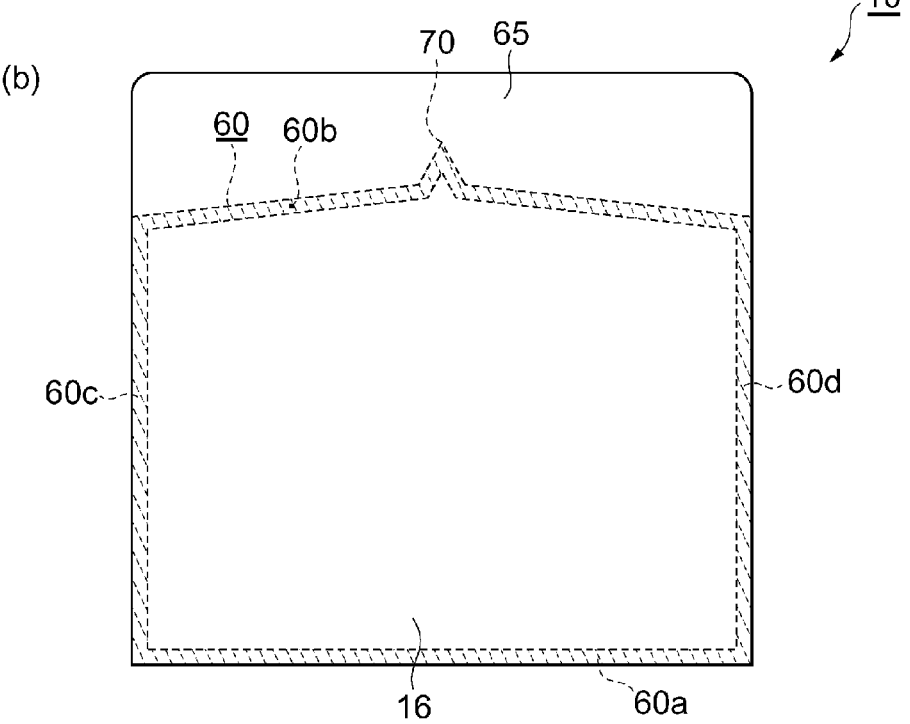

PRESSURE-SENSITIVE ADHESIVE TAPE PACKAGE

This is a National Phase Application filed under 35 U.S.C. §371 as a national stage of PCT/JP2009/071144, filed on Dec. 18, 2009, the content of which is hereby incorporated by reference in its entirety.

TECHNICAL FIELD

The present invention relates to a package for packing an adhesive tape having an adhesive agent layer on a support.

BACKGROUND ART

Adhesive tapes in a variety of forms have conventionally been known and used for labels, medical care, cosmetics, decoration, masking, electronic industries, and other various applications. The adhesive tape used for medical care is in a form of a patch preparation such as a poultice, a plaster, and a surgical tape, and usually applied onto a skin, a mucous membrane, or the like.

Such an adhesive tape usually comprises an adhesive tape having a support and an adhesive agent layer provided on one surface of the support, and a release sheet releasably attached to the adhesive agent layer. The adhesive tape, after production, may be cut into an appropriate size and distributed and sold in the state of being individually contained in a package for hygienic and physical protection. In this case, at the time of use thereof, the adhesive agent layer is applied onto a portion for application after tearing the package to remove the adhesive tape therefrom, and releasing the release sheet off to expose the adhesive agent layer.

A problem that often occurs at the time of use is difficulties in releasing the release sheet. Because the release sheet is usually thin and soft, it is difficult to handle, and it may take some time to release the release sheet. In order to improve this point, for example, as disclosed in Japanese Patent Application Laid-Open Publication Nos. 2007-75602 and 2007-75601, Japanese Patent No. 3689807, Japanese Utility Model Laid-Open No. 50-133797, or the like, a variety of release sheets and adhesive tapes have been developed in which easiness in releasing the release sheet and easiness in applying the adhesive tape are pursued.

Each of these release sheets or adhesive tapes has a structure such that convenience is pursued from the viewpoint of easiness in applying the adhesive tape. It is certainly convenient, but there is no difference in that the adhesive tape maintains the form including the release sheet and the package, and the release sheet and the package are turned into a waste after use.

An object of the present invention is to provide a pressure-sensitive adhesive tape package with which easiness in applying an adhesive tape is pursued while an effect of saving in resources can be obtained.

SUMMARY OF INVENTION

In order to achieve the object, the pressure-sensitive adhesive tape package according to the present invention is a pressure-sensitive adhesive tape package that accommodates an adhesive tape having a support and an adhesive agent layer provided on one surface of the support, the adhesive tape being bent into a first portion and a second portion such that the adhesive agent layer faces outward; the pressure-sensitive adhesive tape package comprising: a first release sheet releasably attached to the adhesive agent layer of the first portion of the adhesive tape, and a second release sheet releasably attached to the adhesive agent layer of the second portion of the adhesive tape to seal the adhesive tape with the first release sheet between the first and second release sheets. By such a configuration, the conventionally existing package can be eliminated. Moreover, since a half of the adhesive agent layer is exposed when by opening the pressure-sensitive adhesive tape package while releasing the first or second release sheet from the adhesive agent layer of the adhesive tape, application to a portion for application is easy.

It is preferable that the first release sheet and the second release sheet are superimposed, and a portion surrounding the adhesive tape in which the first release sheet and the second release sheet are superimposed is sealed. Because the inside is isolated from the outside by sealing between the first and second release sheets, the adhesive tape is protected more hygienically and physically, and no component of the adhesive agent layer of the adhesive tape is leaked to the outside.

It is also effective that at least one projecting point projecting outward is formed in an outer edge of a face-to-face joint portion joining the first release sheet to the second release sheet in a face-to-face relationship to seal therebetween. Because a force concentrates on this projecting point at the time of opening, the face-to-face joint starts breaking from the projecting point to facilitate opening.

It is preferable that a non-bonded portion as a holding portion for opening is provided between the first release sheet and the second release sheet. Moreover, in the case where a mark that can be recognized by touch, like a notch, is provided in the non-bonded portion of one of the first release sheet and the second release sheet, even a visually impaired person can easily figure out the direction of the adhesive agent layer of the adhesive tape to be exposed. It is described as "one of the first release sheet and the second release sheet," and it should be understood that this involves the case where the different kinds of marks are provided in both of the first release sheet and the second release sheet, for example, one notch in the first release sheet and two notches in the second release sheet.

It is preferable that means for reducing an adhesive force that reduces an adhesive force between the adhesive agent layer of the second portion of the adhesive tape and the second release sheet is provided on at least a part of the second release sheet. This is because application to the portion for application is easy as the adhesive surface is exposed when the second release sheet is removed.

The material and configuration of the first release sheet and the second release sheet is not particularly limited as long as the adhesive layer of the adhesive tape can be protected until the adhesive tape is used, but the configuration in which a cellophane film, a plastic film, and an aluminum foil from the outer layer and further a plastic film in the inner layer are laminated is preferable; further, it is preferable that the means for reducing an adhesive force is a silicone-treated surface provided on at least a part of a portion of the second release sheet that is applied to the adhesive agent layer of the second portion of the adhesive tape. Among a variety of means for reducing an adhesive force, the silicone treatment is advantageous in that the treatment is performed relatively easily and at low cost. As another means for reducing an adhesive force, embossing and/or sanding may be performed on the portion.

As other means for easily releasing the second release sheet from the adhesive agent layer of the adhesive tape, in a portion of the first release sheet in which the second portion of the adhesive tape is larger than the first portion of the adhesive tape, and has an extending portion that extends from the first portion, a temporary attaching means may be provided in at least a part of a portion facing the extending portion in a portion of the release sheet on the second portion side of the adhesive tape. It is preferable that an adhesive force of the support of the adhesive tape to the first release sheet through the temporary attaching means is larger than an adhesive force of the adhesive agent layer to the second release sheet. As the temporary attaching means, an adhesive agent, namely, those having adhesiveness to the support of the adhesive tape are preferable. By providing such a temporary attaching means in the first release sheet, the second portion of the adhesive tape is easily separated from the second release sheet without a silicone-treated surface or the like, and it is more preferable that provision of the temporary attaching means is used in combination with the silicone-treated surface or the like.

The first portion and the second portion of the adhesive tape may be substantially in the same shape, and the temporary attaching means may be provided between the first portion and the second portion. In this case, it is preferable that the adhesive force or attaching force of the temporary attaching means is larger than the adhesive force of the adhesive agent layer to the release sheet.

The thus-configured pressure-sensitive adhesive tape package can apply the whole surface of the adhesive tape to the portion for application by adhering an exposed portion of the adhesive agent layer of the adhesive tape that appears at the same time when the second release sheet is removed to the portion for application, and then pulling the first release sheet in a direction in which the adhesive tape is released from the first release sheet.

ADVANTAGEOUS EFFECTS OF INVENTION

According to the pressure-sensitive adhesive tape package of the present invention, a pressure-sensitive adhesive tape package that can be applied to all other adhesive tape as long as the adhesive tape has a release sheet and is an adhesive tape in a form of individual packaging, and is resource saving and easy to apply is provided. Namely, the pressure-sensitive adhesive tape package of the present invention can eliminate the conventionally existing individual package, and the adhesive tape is hygienically and physically protected because at the time of storing the adhesive tape, the first release sheet and the second release sheet are sealed to isolate the inside from the outside even if the package is eliminated.

Moreover, since a half of the adhesive agent layer is exposed, at the time of using the adhesive tape, by removing the release sheet while releasing the second release sheet from the adhesive agent layer of the adhesive tape, application to the portion for application is easy. Additionally, after the second release sheet is released, the adhesive tape is supported or reinforced on the first release sheet; for this reason, this prevents the adhesive tapes from adhering to each other to cause a state where the patch preparation cannot be used, and application is easy. Moreover, in the case where the adhesive tape is a patch preparation that can be applied to a human body, such as a plaster, a poultice, a surgical tape, an adhesive heating pack or the like, the adhesive tape can be easily applied by a single hand without getting a hand dirty even if the portion for application is a back or the like in which application is difficult by oneself.

Moreover, according to the pressure-sensitive adhesive tape package of the present invention, the temporary attaching means is provided between the first release sheet and the support of the adhesive tape; thereby, without a silicone-treated surface or the like, the second portion of the adhesive tape is easy to be separated from the second release sheet to easily expose an half of the adhesive agent layer.

The pressure-sensitive adhesive tape package of the present invention is made into a product as a single unit; accordingly, portable convenience is high.

BRIEF DESCRIPTION OF DRAWINGS

FIGS. 3(a) to 3(d) are drawings illustrating a shape of an edge of the release sheet.

FIGS. 4(a) to 4(c) are perspective views showing a method using the pressure-sensitive adhesive tape package according to the present invention.

FIGS. 8(a) and 8(b) are perspective views showing an example of a form that facilitates opening

FIGS. 11(a) and 11(b) are schematic explanatory views showing a modification of the second embodiment of the present invention.

DESCRIPTION OF EMBODIMENTS

Figure 1:
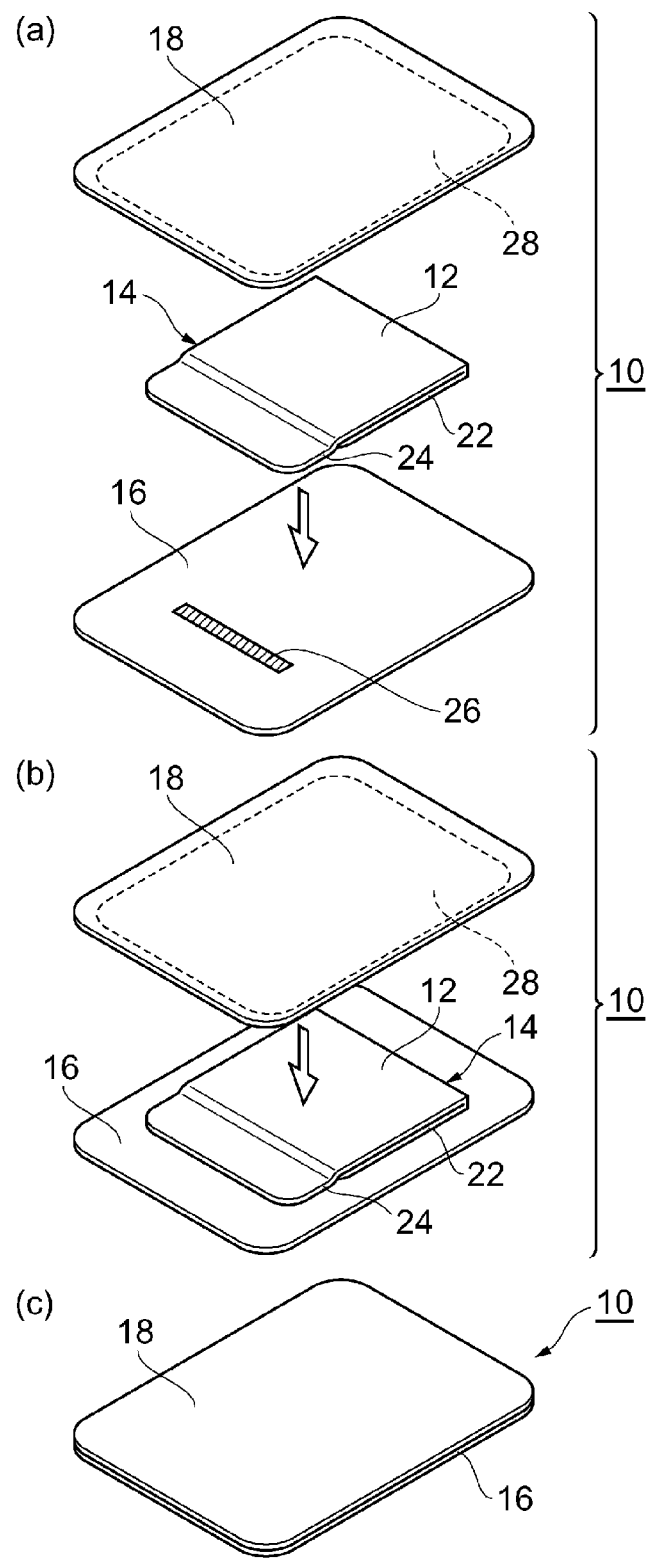
FIGS. 1(a) to 1(c) are perspective views showing production steps of a pressure-sensitive adhesive tape package according to a first embodiment of the present invention.

Hereinafter, with reference to the drawings, suitable embodiments according to the present invention will be described. Through all the drawings, same reference numerals will be given to same or equivalent portions, and the duplicate description thereof will be omitted.

[First Embodiment]

FIGS. 1(a) to 1(c) are perspective views showing the production steps of a pressure-sensitive adhesive tape package 10 according to the present invention. The pressure-sensitive adhesive tape package 10 includes an adhesive tape 14 having an adhesive agent layer 12 on one surface thereof (see FIG. 2), a first release sheet 16 bent into two in a shape such that the entire adhesive tape 14 may be covered, as described later, and a second release sheet 18 in the same shape as that of the first release sheet. It is preferable that the adhesive tape 14, the first release sheet 16, and the second release sheet 18 are each rectangular.

Figure 2:
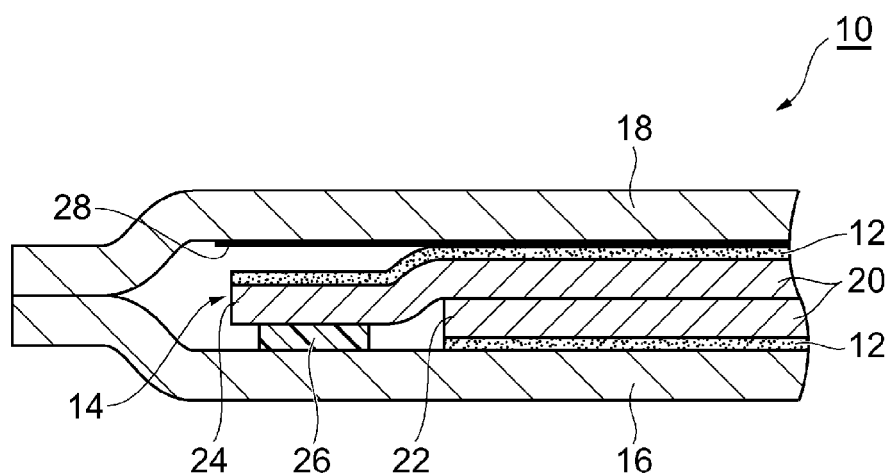
FIG. 2 is a drawing showing part of a cross section of the pressure-sensitive adhesive tape package according to the present invention.

FIG. 2 is a drawing showing part of a cross section of the pressure-sensitive adhesive tape package 10. The first release sheet 16 is releasably attached to the adhesive agent layer 12 of the first portion 22 and the second release sheet 18 is releasably attached to the adhesive agent layer 12 of the second portion 24 in the adhesive tape 14 provided on the one surface of the support 20 and bent into two such that the adhesive agent layer 12 may face outward.

The pressure-sensitive adhesive tape package of the present invention is used for labels, medical care, cosmetics, decoration, masking, electronic industries, and other various applications. Particularly, the pressure-sensitive adhesive tape package used for medical care, cosmetics, and the like can be used as a package of a patch preparation such as a poultice, a plaster, a surgical tape, a cosmetic face pack preparation, and an adhesive heating pack that is usually applied to a skin, a mucous membrane, and the like.

The component material of the support 20 is not particularly limited as long as it can support the adhesive agent layer 12, and usually, woven fabrics, non-woven fabrics, films made of a plastic or the like, metallic foils, and the like are used. Further, the support may be a single layer structure or a laminate structure; it may be a structure in which a plurality of woven fabrics or non-woven fabrics made of different materials is laminated, or a structure in which a plastic film, a metallic foil, or the like and a woven fabric or a non-woven fabric are laminated, for example.

Moreover, the woven fabric or non-woven fabric used for the present invention is not particularly limited, and may be those obtained by processing a fibrous material into a fabric and applicable for the support of the adhesive tape; examples thereof include a knitted fabric processed into a fabric by collecting stitches by circular knit, warp knit, weft knit, and the like.

Preferable examples of the woven fabric or non-woven fabric include woven fabrics or non-woven fabrics made of at least one kind of resin fibers selected from the group consisting of polyester resins, polyethylene resins, and polypropylene resins; among them, the woven fabrics made of polyethylene terephthalate that is polyester with less interaction with the component contained in the adhesive agent layer are preferable.

Examples of the plastic film include those formed using polyesters such as polyethylene terephthalate, polyamides such as nylon, polyolefins such as polyethylene and polypropylene, polyvinyl chloride, plasticized polyvinyl chloride, plasticized vinyl acetate-vinyl chloride copolymers, polyvinylidene chloride, ethylene-vinyl acetate copolymers, cellulose acetate, ethyl cellulose, ethylene-ethyl acrylate copolymers, polytetrafluoroethylene, polyurethanes, and ionomer resins. Moreover, in the case where the adhesive tape of the present invention is used as the patch preparation for medical care or cosmetics, it is preferable that a material having sufficient stretchability or non-stretchability as a patch preparation is used for the support, and a polyethylene terephthalate hosiery woven fabric (knitted fabric) is particularly preferable.

It is preferable that in the knitted fabric as the support 20, the basis weight (mass per units) is 50 to 500 g/m$^2$. Moreover, in the case where the support 20 is measured according to the method of JIS L1018, it is preferable that the modulus in the longitudinal length (long axis direction) is 2 to 12 N/5 cm, and the modulus in the traverse direction (short axis direction) is also 2 to 12 N/5 cm. The longitudinal length here refers to a flow direction at a step of producing a knitted fabric, and the traverse direction refers to a direction perpendicular to the longitudinal length, namely the width direction. In the case where the modulus is smaller than 2 N/5 cm in the longitudinal length or traverse direction, application to the portion for application while unwrinkling tends to be difficult; moreover, in the case where the modulus is larger than 12 N/5 cm in the longitudinal length or traverse direction, conversely, the adhesive tape tends to be excessively stretched during application to cause wrinkles. The modulus is a value at room temperature (25° C.).

By use of the support 20 above, temporary attaching by the temporary attaching means described later is facilitated, and the shape and structure of the support 20 after the support is removed from the temporary attaching are hardly changed. Namely, fuzzing or the like is not produced, for example. Moreover, bending the pressure-sensitive adhesive tape package 10 into two is easy, and the bent pressure-sensitive adhesive tape package is not bulky. Further, the so-called "kink" is hardly produced in the portion that is bent into two during application, and the adhesive tape is applied neatly.

The adhesive component that is the component material of the adhesive agent layer 12 is not particularly limited as long as it has adhesiveness and can be applied to the portion for application; acrylic adhesive components, rubber based adhesive components, silicone based adhesive components, and the like are preferably used as an adhesive base; among them, the rubber based adhesive components are particularly preferably used from the viewpoint of adhesiveness.

As a specific example of the rubber based adhesive component, natural rubbers and synthetic rubbers both can be used, and examples of the synthetic rubbers include styrene block copolymers and polyisobutylene. Further, examples of the styrene block copolymers include styrene-butylene-styrene block copolymers (SBS), styrene-isoprene-styrene block copolymers (SIS), styrene-ethylene/butylene-styrene block copolymers (SEBS), and styrene-ethylene/propylene-styrene block copolymers (SEPS).

Specific examples of the styrene block copolymers include linear triblock copolymers such as Kraton D-1112, D-1111, and D-1107 (trade name, made by Kraton Performance Polymers Inc), JSR5000 or JSR5002 (trade name, made by JSR Corporation), Quintac 3530, 3421 or 3570C (trade name, made by Zeon Corporation), and Kraton D-KX401CS or D-1107CU (trade name, made by Kraton Performance Polymers Inc), and branched block copolymers such as Kraton D-1124 (trade name, made by Kraton Performance Polymers, Inc.) and Solpren 418 (trade name, made by Phillips Petroleum Company).

As polyisobutylene, for example, polymers thereof and those of low molecular weight are used, and examples thereof include Oppanol 10, 12, 12SF, 15, 15SF, 30SF, 50, 50SF, 80, 100, 120, 150, and 200 (trade name, made by BASF SE), and Vistanex LM-MS, LM-MH, LM-H, MM L- 80, MM L- 100, MM L- 120, and MM L- 140 (trade name, made by Exxon Chemical Company).

Moreover, as the acrylic polymer, a polymer or copolymer containing at least one (meth)acrylate ester such as 2-ethylhexyl acrylate, methyl acrylate, butyl acrylate, hydroxyethyl acrylate, 2-ethylhexyl-methacrylate as a monomer unit is used, and acrylic acid/acrylic acid octyl ester copolymers, 2-ethylhexyl acrylate/N-vinyl-2-pyrrolidone/1,6-hexaneglycol dimethacrylate copolymers, 2-ethylhexyl acrylate/vinyl acetate copolymers, 2-ethylhexyl acrylate/vinyl acetate/acrylic acid copolymers, 2-ethylhexyl acrylate/ 2-ethylhexyl-methacrylate/dodecyl methacrylate copolymers, a methyl acrylate/2-ethylhexyl acrylate co polymerized resin emulsion, an adhesive agent of an acrylic polymer or the like contained in an acrylic resin alkanolamine solution, Duro-Tak acrylic adhesive agent series (made by National Starch and Chemical Company), GELVA acrylic adhesive agent series (made by Monsanto Company), SK-Dyne Matriderm (Soken Chemical & Engineering Co., Ltd.), EUDRAGIT series (Higuchi Inc.), and the like can be used, for example.

One of the adhesive bases such as the rubber adhesive base, the acrylic adhesive base, and the silicone adhesive base above can be used, or two or more thereof can be mixed and used.

Further, in the case where the adhesive tape of the present invention is used as a poultice or a plaster for medical care or a cosmetic face pack agent, a water-soluble polymer can also be used as the adhesive agent layer; as such a water-soluble polymer, gelatin, agar, alginic acid, mannan, carboxymethyl cellulose or salts thereof, hydroxypropyl cellulose or salts thereof, polyvinyl alcohol, polyacrylic acid or salts thereof, and the like, or those obtained by crosslinking at least one of these by an organic or inorganic crosslinking agent are preferably used.

Other than the adhesive bases above, a tackifier, a softening agent, a solvent, water, a thickener, a wetting agent, a filler, a crosslinking agent, a polymerizing agent, a solubilizing agent, an absorption promoter, a stabilizer, an antioxidant, an emulsifier, a surface active agent, a pH adjuster, drugs, an ultraviolet absorbing agent, and the like are properly added to the adhesive agent layer.

The drugs in the case where the adhesive tape of the present invention is used as the patch preparation for medical care and cosmetics are not particularly limited as long as they are percutaneously absorbed into the body to demonstrate a pharmacological effect, and examples thereof include an antiinflammatory agent, an analgesic agent, an antihistamine, a local anesthetic agent, a blood circulation promoter, an anesthetic agent, a tranquilizer, an antihypertensive agent, an antibacterial agent, and a vasodilator.

The first release sheet 16 and the second release sheet 18 of the present invention can be used if they are those usually used as the package of the adhesive tape. Moreover, the first release sheet 16 and the second release sheet 18 may be a single layer or a laminated layer, and the material that forms the release sheet is not particularly limited if the advantageous effects of the present invention are obtained. For example, the material can be properly selected from paper, a non-woven fabric, aluminum, cellophane, nylon, high density or low density polyethylene, polyethylene terephthalate, polypropylene, polyvinyl chloride, polyamide, polyvinylidene chloride, polyvinyl alcohol, polyvinyl acetate copolymers, polycarbonate, polystyrene, ethylene vinyl alcohol copolymers, and the like.

Further, the release sheet may be those in which a printing ink or an adhesive is applied, or those on which a thin film is provided by a method such as deposition or sputtering. As the thin film, thin films with high gas barrier properties and transparency made of silicon oxide, magnesium oxide, and aluminum oxide other than metals such as aluminum are suitable. Among these, the film containing aluminum is preferable, those in which further polyethylene, aluminum, polyethylene are sequentially laminated are more preferable, and those in which cellophane is also further laminated on the outermost layer are preferable for use.

For these release sheets, those having flexibility are preferable. Accordingly, the thickness of the release sheet is not particularly limited, and it is preferable that the thickness is in the range of 10 to 500 μm, and it is more preferable that the thickness is in the range of 15 to 300 μm.

As shown in FIG. 1(a), the adhesive tape 14 sealed by the first release sheet 16 and the second release sheet 18 is bent into the first portion 22 and the second portion 24 along a line parallel to the short direction of the adhesive tape 14 (bending line) such that the adhesive agent layer 12 may face outward. The second portion 24 is larger than the first portion 22, and in the second portion 24, a extending portion that extends from the first portion 22 exists.

In the adhesive tape 14 thus bent into two, the first release sheet 16 is releasably attached to the first portion 22 of the adhesive tape 14 to provide the state in FIG. 1(b). At this time, the extending portion of the second portion 24 is temporarily attached by a temporary attaching means 26 provided in a portion on the first release sheet 16 facing the extending portion (see FIG. 2).

Next, the second release sheet 18 subjected to a silicone treatment 28 described later is releasably attached to the second portion 24 of the adhesive tape 14 to seal the adhesive tape 14 between the first release sheet 16 and the second release sheet 18; thereby, the pressure-sensitive adhesive tape package 10 of the present invention is finished (FIG. 1(c)).

As a method for sealing the adhesive tape 14, a method for sealing a portion surrounding the adhesive tape 14 in the portion where the first release sheet 16 and the second release sheet 18 are superimposed is preferable. By sealing between the release sheets 16 and 18, the inside is isolated from the outside; for this reason, the adhesive tape 14 is more hygienically and physically protected, leading to advantages such that no component contained in the adhesive agent layer of the pressure-sensitive adhesive tape package 10 is leaked to the outside, volatilized or the like.

As a method for sealing the periphery of the first release sheet 16 and the second release sheet 18 which are superimposed, other than a heat sealing method, a method using an adhesive and the like can be considered. Alternatively, the periphery of both of the release sheets may be fixed by a tape. By the pressure-sensitive adhesive tape package 10 thus configured, the first release sheet 16 and the second release sheet 18 also function as a package; accordingly, a conventionally existing separate package can be eliminated.

In order to avoid a pointed corner of the finished pressure-sensitive adhesive tape package, it is preferable that the first release sheet 16 and the second release sheet 18 have an approximately rectangular shape such that part of the corners and preferably all four corners of the finished pressure-sensitive adhesive tape package may be in a round shape as shown in FIG. 1(c).

Further, other means can be used so as not to hurt the portion for application or the surrounding thereof during application by an edge of the release sheets, for example, like all or part of edges of the first release sheet 16 and the second release sheet 18 can be formed into a wave form, a pulse form, or a band shape, or the leading end of the edge is intendedly not bonded (see FIGS. 3(a) to 3(d)).

In the present invention, it is preferable that the second release sheet 18 has means for reducing an adhesive force that reduces an adhesive force between the adhesive agent layer 12 of the second portion of the adhesive tape 14 and the second release sheet 18. As this means for reducing an adhesive force, it can be considered that the whole surface of the second release sheet 18 is subjected to a releasing treatment, while only the portion shown in FIGS. 1(a) and 1(b) and by the reference numeral 28 in FIG. 2 may be subjected to a releasing treatment. Moreover, this means for reducing an adhesive force aims at making a second portion 24 of the adhesive tape 14 be easily released from the second release sheet 18 at the time of opening the pressure-sensitive adhesive tape package 10; for this reason, only a portion of the second release sheet 18 that the second portion 24 of the adhesive tape 14 contacts may be subjected to the releasing treatment, or only a part of the portion may be subjected to the releasing treatment as long as the purpose can be attained.

Examples of the releasing treatment include, other than a method using a release agent, a method such as embossing and sanding that physically makes releasing easy. As the release agent, any of silicone release agents, alkyl pendant release agents, condensed wax release agents, and the like can be used; among these, the silicone treatment using the silicone release agent is preferable. The silicone treatment is advantageous in that it is performed relatively easily and at low cost. By performing the silicone treatment, upon use of the pressure-sensitive adhesive tape package 10, when the second release sheet 18 is removed, the adhesive agent layer 12 is easily removed from the second release sheet 18 to expose the adhesive agent layer 12; for this reason, application to the portion for application is easy.

As other means for easily releasing the second release sheet 18 from the adhesive agent layer 12 of the adhesive tape 14, means for temporarily holding at least a part of the support 20 of the adhesive tape 14, namely a temporary attaching means can be provided in the first release sheet 18. The temporary attaching means is not particularly limited, and other than a magnetic force, an electrostatic force, or a physical force such as a magic tape, a double-sided adhesive tape, an adhesive agent, and an adhesive, pseudoadhesion, welding, thermal bonding, hard pressing, pressing, and a hot-melt adhesive according to the material, shape or the like of the first release sheet 16 or the support 20, and the like can be used, for example. Particularly, in the case where the inner layer of the first release sheet 16 is composed of a thermoplastic material that melts at a predetermined temperature, and the support 18 of the adhesive tape 14 is formed of a woven fabric, for example, the inner layer of the release sheet 16 can be molten to be permeated into the woven fabric of the support 18, and solidified there; accordingly, temporary attaching by thermal bonding is effective. Moreover, even in the case where the release sheet 16 is not thermoplastic, it can be considered that the thermoplastic material is contained in the material of the support 18 thereby to perform thermal bonding. Moreover, the inner surface of the first release sheet 16 is embossed to form a number of projected portions, and means for holding the support 20 by hooking the support 18 to these projected portions can also be used.

While a variety of temporary attaching means described above can be used, among them, the method using pseudoadhesion or a hot-melt adhesive or a method using thermal bonding are particularly preferable. In the method using pseudoadhesion or a hot-melt adhesive, the adhesive tape 14 is bent along the bending line into the first portion 22 and the second portion 24 so that the adhesive agent layer faces outward, the second portion 24 is larger than the first portion 22, the second portion 24 has an extending portion that extends from the first portion 22, and pseudoadhesion or a hot-melt adhesive is used in a portion 26 facing the extending portion in a portion of the first release sheet 16. The adhesive force of the adhesive portion 26 to the support 20 of the adhesive tape 14 is larger than the tackiness of the adhesive agent layer 12 to the second release sheet 18; thereby, without means for reducing an adhesive force 28 such as a silicone-treated surface or the like, the second portion 24 of the adhesive tape 14 is easily separated from the second release sheet 18 upon use of the pressure-sensitive adhesive tape package 10. It is more preferable that formation of such an adhesive portion 26 is used in combination of the silicone-treated surface 28.

On the other hand, in the case of the temporary attaching by thermal bonding, no portion 26 as described above is formed. It should be understood that in the temporary attaching by thermal bonding, after or at the same time when the first release sheet 16 and the second release sheet 18 are superimposed into the state in FIG. 1(*c*), the outer periphery of the portion in which the first release sheet 16 and the second release sheet 18 are superimposed is sealed, for example, heat-sealed, thermal bonding may be performed. Alternatively, after thermal bonding, the outer periphery of the first release sheet 16 and the second release sheet 18 may be sealed by heat sealing or the like.

The temporary attaching means may be those in which the adhesive force of the support 20 of the adhesive tape 14 to the first release sheet 16 (the adhesive force of the adhesive portion 26 as the temporary attaching means) is larger than the adhesive force (tackiness) of the adhesive agent layer 12 to the second release sheet 18. Namely, the adhesive force of the support 20 to the first release sheet 16 through the temporary attaching means, the adhesive force (tackiness) of the adhesive agent layer 12 of the adhesive tape 14 to the portion for application, and the adhesive force of the adhesive agent layer 12 of the adhesive tape 14 to the second release sheet 18 are in a relation as follows.

the adhesive force of the adhesive agent layer 12 to the portion for application
>the adhesive force of the support 20 to the first release sheet 16 through temporary attaching means
>the adhesive force of the adhesive agent layer 12 to the second release sheet 18

The pseudoadhesion refers to those that usually have no adhesiveness or tackiness, but bond objects on a special process condition or the like as described in the Patent Map for Technical Fields, General 21 "Adhesion," p. 336, available from the Japan Patent Office website mentioned below, and a pseudoadhesive prepared by adding an additive to an adhesive agent is used. As the pseudoadhesive, various known pseudoadhesives can be used. Such a pseudoadhesive may be applied to the portion facing the extending portion in a portion of the first release sheet 16; it may be provided in dots, applied to the whole surface of the extending portion of the support 20, or provided on the extending portion in lines or dots. Moreover, the pseudoadhesive is not applied, and a pseudoadhesive resin layer may be formed at a necessary place.

Hereinafter, with reference to FIGS. 4 to 7, the action and effect of the pressure-sensitive adhesive tape package 10 according to the present embodiment will be described.

FIG. 4(*a*) shows a perspective view of the pressure-sensitive adhesive tape package 10 according to the present embodiment. Comparing to the conventional adhesive tape, the pressure-sensitive adhesive tape package 10 according to the present embodiment has no package separated from the release sheet, and therefore, is resource saving. The pressure-sensitive adhesive tape package of the present invention 10 is made into a product as a single unit, and therefore, portable convenience is high.

FIG. 4(*b*) shows a state where the second release sheet 18 starts being removed from one end of the portion of the sealed periphery of the first release sheet 16 and the second release sheet 18. The second release sheet 18 is removed while being released from the adhesive agent layer 12 of the second portion 24 of the adhesive tape 14.

Then, as shown in FIG. 4(*c*), when the second release sheet 18 is completely removed, the adhesive agent layer 12 of the second portion 24 of the adhesive tape 14 is exposed. Particularly, in the case where the second release sheet 18 is subjected to the silicone treatment that reduces the adhesive force between the adhesive agent layer 12 of the second portion 24 of the adhesive tape 14 and the second release sheet 18, the state of FIG. 4(*c*) can be easily obtained. Further, in the case where the temporary attaching means 26 such as the pseudoadhesive or a hot-melt adhesive is provided in the first release sheet 16, the state of FIG. 4(c) can be easily obtained without a silicone-treated surface if the adhesive force of the support 20 of the adhesive tape 14 to the first release sheet 16 through the temporary attaching means is designed so as to be larger than the adhesive force of the adhesive agent layer 12 to the second release sheet 18.

Figure 5:
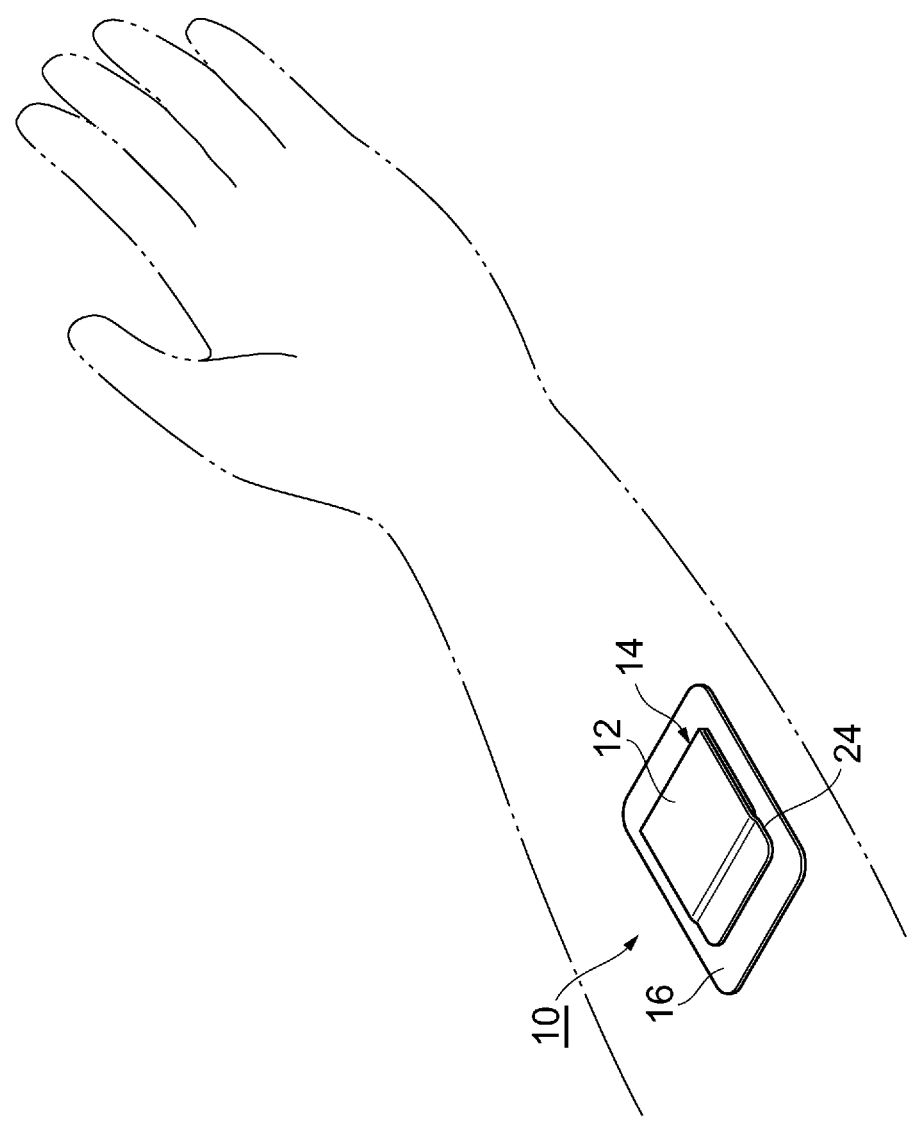
FIG. 5 is a drawing showing a scene in which the adhesive tape according to the present invention is applied to a portion for application.
Figure 6:
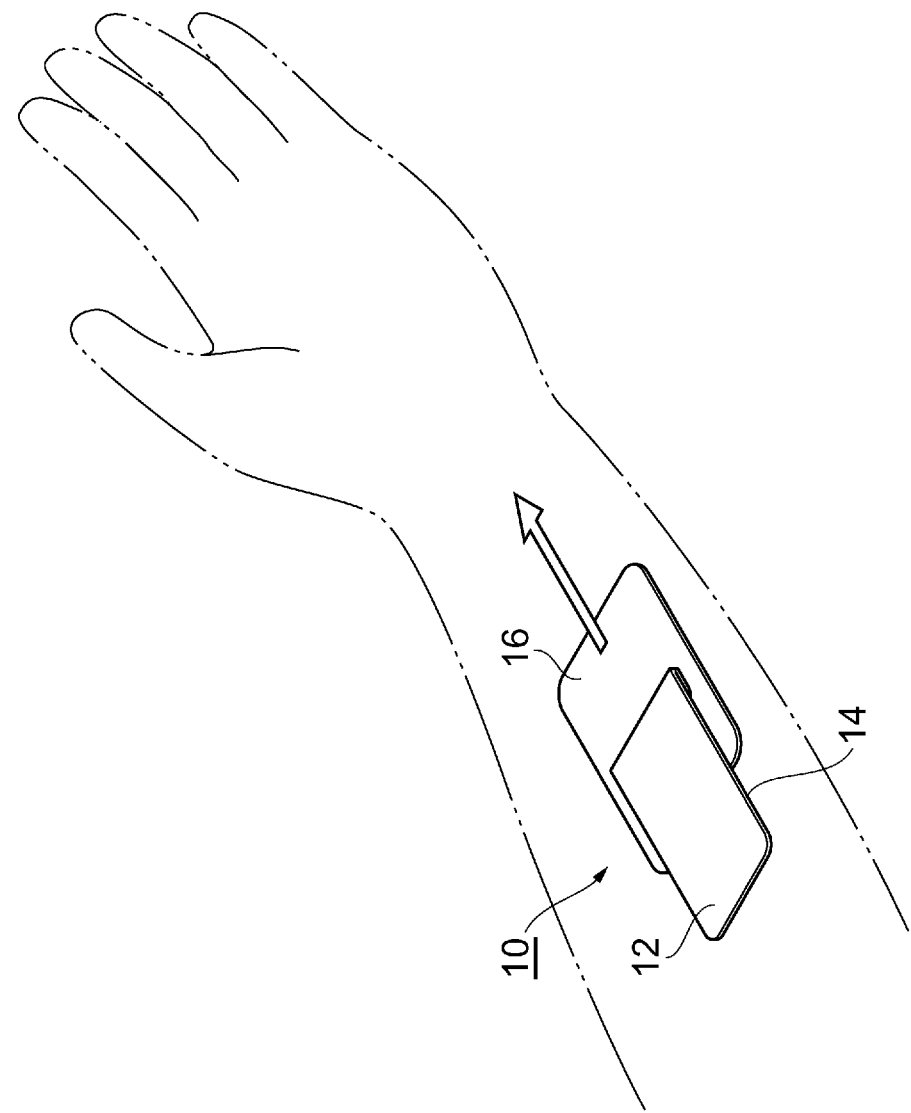
FIG. 6 is a drawing of a scene in which the adhesive tape according to the present invention is applied to a portion for application, and is a drawing showing the state continuing from FIG. 4.
Figure 7:
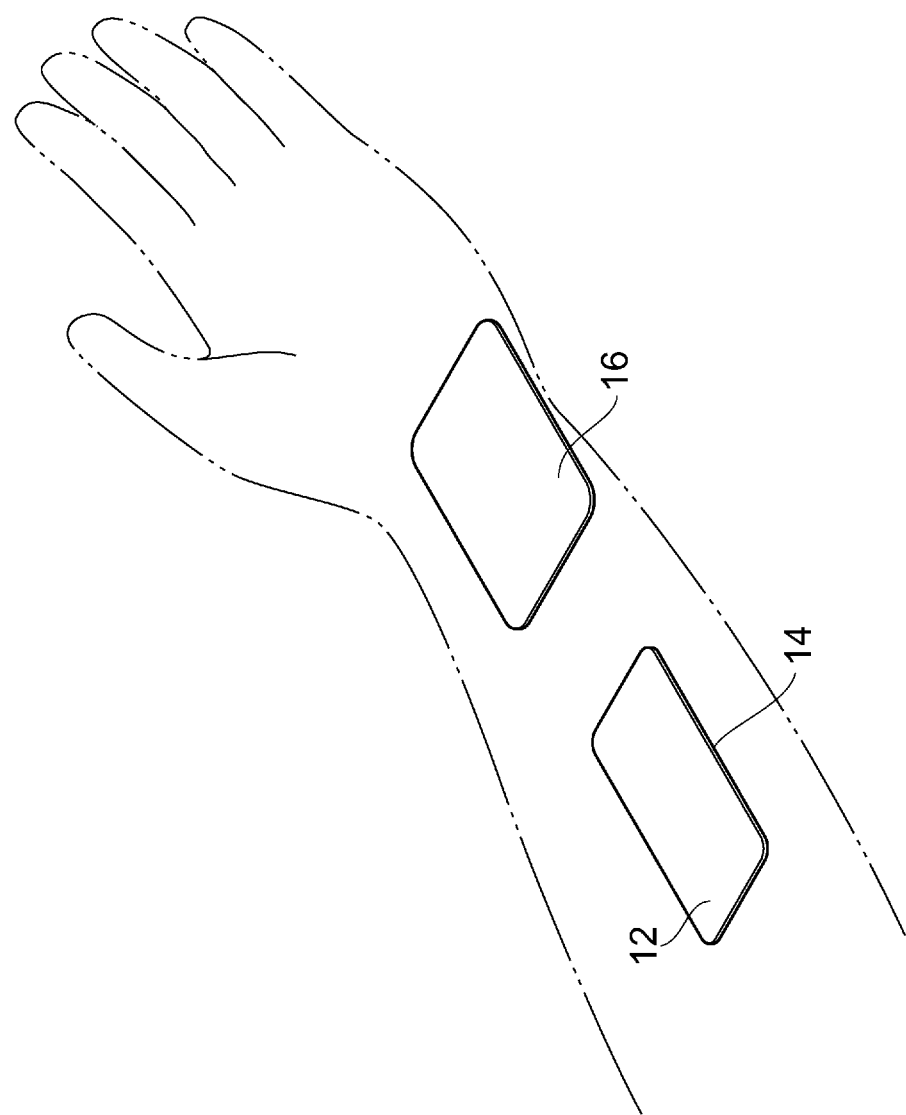
FIG. 7 is a drawing showing a state where application of the adhesive tape according to the present invention to the portion for application is finished.

FIGS. 5 to 7 show aspects in the case where the adhesive tape of the present invention is used particularly as the patch preparation for medical care or cosmetics, while the adhesive tape of the present invention can also be applied by the same method in the case of use in other application. Namely, FIGS. 5 to 7 show a method for applying to the portion for application a pressure-sensitive adhesive tape package in which the adhesive agent layer 12 of the first portion 22 of the adhesive tape 14 is exposed. First, the pressure-sensitive adhesive tape package is held by one hand, and placed in the portion for application or in the vicinity of the portion for application as shown in FIG. 5. Next, as shown in FIG. 6, while the first release sheet 16 is held by hand, the first release sheet 16 is pulled along the skin in a direction in which the adhesive tape 14 is released from the first release sheet 16. As the first release sheet 16 is pulled away, the first portion 22 of the adhesive tape 14 is released from the first release sheet 16 and simultaneously applied to the portion for application. Particularly, because the adhesive tape 14 is applied while the first release sheet 16 is pulled, the adhesive tape 14 can be applied without a wrinkle. FIG. 7 shows the state where the whole adhesive tape 14 is applied to the portion for application to finish application.

The adhesive tape of the present invention can be held by hand because the periphery of the first release sheet 16 having been superimposed with the second release sheet 18 can be supported by the thumb of the hand on which the adhesive tape is placed. Accordingly, a risk of dropping the adhesive tape when the adhesive tape is applied to the portion for application is small, and worries about shifting of the adhesive tape or hanging of the adhesive tape by gravity in an unintended direction during application are small; for this reason, the adhesive tape can be applied to the portion for application to be targeted for in a carefree manner. The adhesive tape can be easily applied by a single hand even if the portion for application is a back or the like in which application is difficult by oneself.

In the use operation above, a risk of contact of the adhesive agent layer with a skin other than the portion for application is small. Without sticking of the adhesive agent layer to the fingers and hands that is often experienced in use of the conventional adhesive tape, it is hygienical; after the second release sheet is removed, the adhesive tape is supported or reinforced on the first release sheet, therefore preventing the state where the patch preparation cannot be used by adhesion of the adhesive agents to each other.

By the way, in order to facilitate opening the pressure-sensitive adhesive tape package 10, as means for sealing the periphery of the first release sheet 16 and the second release sheet 18, use of the so-called easy peel techniques is effective. The easy peel means easy releasability as described in the Patent Map for Technical Fields, General 21 "Adhesion," p. 335, available from the Japan Patent Office website (www.jpo.go.jp/shiryou/s_sonota/map/ippan21/4/4-3-1.htm), and refers to containers and packages sealed by heat sealing to provide easy releasing upon opening. Specifically, examples of easy peel include various types such as an aggregation releasing type in which the adhesive layer between the first release sheet 16 and the second release sheet 18 itself is broken to be released, an interlayer releasing type in which adhesive strength between the adhesive layer and the first release sheet 16 or the second release sheet 18 is small, and the first release sheet 16 or the second release sheet 18 is released from the adhesive layer at the time of opening, and an interface releasing type using an easy-releasable resin such as EVA, but are not particularly limited thereto; in the case where a sheet material in which a polyethylene layer is disposed on the surface is used as the first and second release sheets 16 and 18, those with a two-layered structure composed of a resin layer containing a high density polyethylene as a principal component and an easy-peel resin layer prepared by adding a resin causing aggregation breakage to a low density polyethylene, for example, may be used as an easy peel adhesive layer.

Further, provision of a notch in an edge for easy removal of the second release sheet 18, or provision of a fragile portion for opening in the first release sheet 16 and the second release sheet 18 can be properly used.

Moreover, for the same purpose, as shown in FIGS. 8(a) and 8(b), the end portions of the first release sheet 16 and the second release sheet 18 may be left not bonded such that non-bonded portions 30 may be held. Particularly, in the case of the shape shown in FIG. 8(b), wider non-bonded portions 30 can be provided to be held more easily. Of course, by use of the easy peel techniques above in combination, opening is easier.

Figure 9:
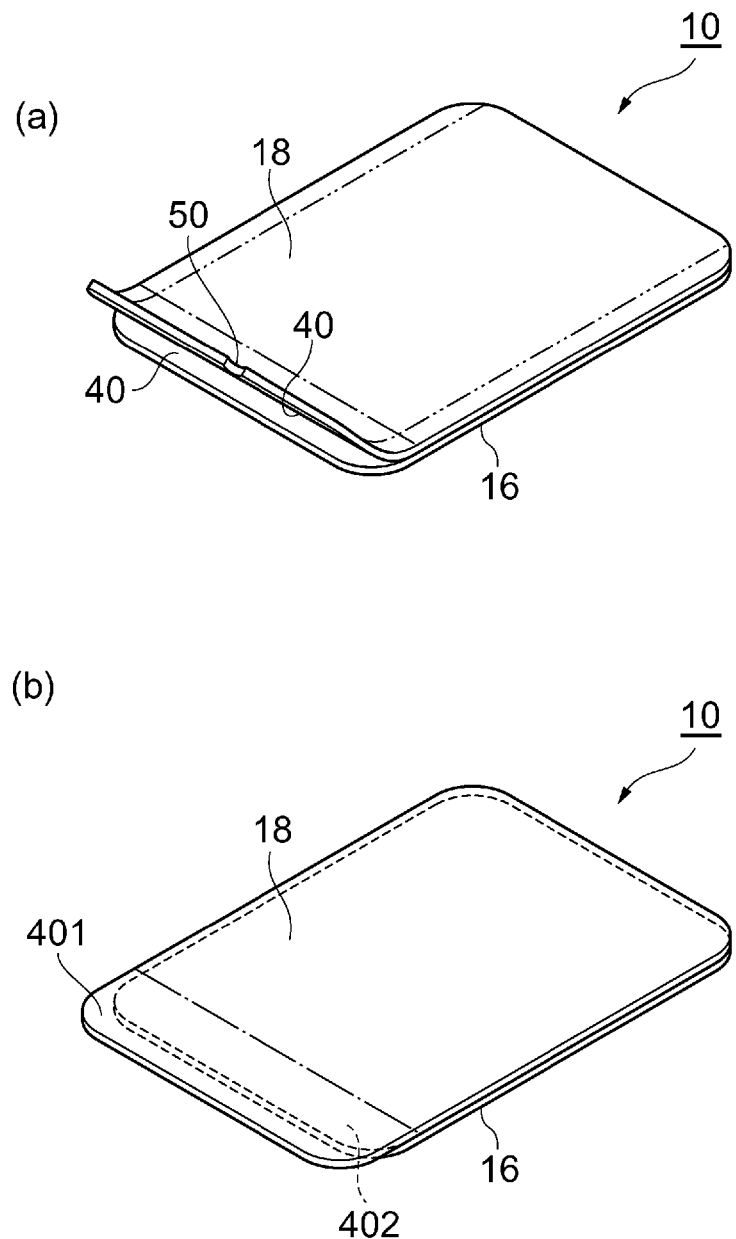
FIGS. 9(a) and 9(b) are perspective views showing further other example of a form that facilitates opening

Further, the pressure-sensitive adhesive tape packages 10 shown in FIGS. 9(a) and 9(b) are examples of easy opening; the entire end portions of the first release sheet 16 and the second release sheet 18 may be left not bonded such that the non-bonded portions 40 may be held. This case is advantageous in that the non-bonded portions 40 are easy to hold because the area of the non-bonded portions 40 ranging across the width of the package 10 is large. Moreover, similarly to the description above, the sealed portion (portion of the long dashed short dashed line) is subjected to the easy peel to further facilitate opening; however, if the portion shown by the long dashed double-short dashed line in FIG. 9(a) is formed as a line of weakness by heating, for example, the sealed portion is easily cut across along the line of weakness to cut off the first release sheet 16 into a desired shape without easy-peeling the sealed portion.

Moreover, as shown in FIG. 9(a), it is also preferable that a mark 50 such as a notch that can be recognized by touch is provided in one of the first and second release sheets 16 and 18, for example, an edge of the non-bonded portions 40 of the first release sheet 18. In the present invention, when the pressure-sensitive adhesive tape package 10 is opened, the adhesive agent layer 12 of the adhesive tape 14 facing upward is convenient for application operation as described later (see FIG. 4(c)); however, by providing the mark 50 that can be recognized by touch in at least one of the first and second release sheets 16 and 18, even a visually impaired person can recognize the top and bottom of the package 10. It can be thought that the mark 50 that can be recognized by touch may be a variety of objects such as a shape shown in FIG. 3, embossing, and projection other than the notch.

The configuration of FIG. 9(b) is one type thereof, in which the non-bonded portion 401 of the first release sheet 16 is longer than the non-bonded portion 402 of the second release sheet 18 such that the top and bottom of the package can be recognized by touch. Needless to say, such a mark can also be applied to the configuration shown in FIG. 8. As shown in FIG. 9(b), the edge of the non-bonded portion 401 of the first release sheet 16 is positioned off from that of the non-bonded portion 402 of the second release sheet 18 to provide a height difference; thereby, an effect of holding the non-bonded portion 401 much more easily is obtained.

[Second Embodiment]

Figure 10:
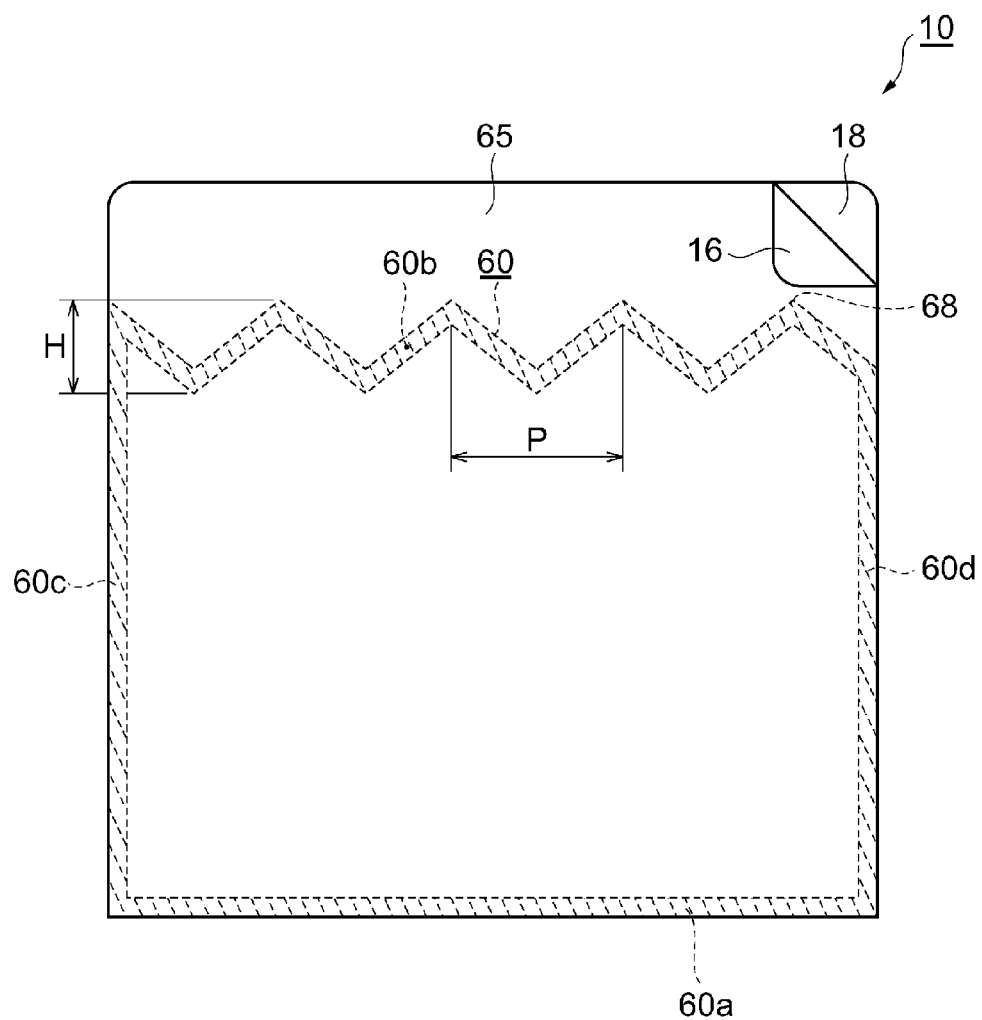
FIG. 10 is a schematic explanatory view showing a pressure-sensitive adhesive tape package according to a second embodiment of the present invention.

FIG. 10 is a schematic explanatory view showing a pressure-sensitive adhesive tape package 10 devised in order to further facilitate opening. The pressure-sensitive adhesive tape package 10 shown in FIG. 10 is characterized by the shape of a heat-sealed portion 60 in the portion in which the first release sheet 16 and the second release sheet 18 are superimposed. Other configuration is the same as that in the first embodiment above, and the description thereof will be omitted.

As shown in FIG. 10, the heat-sealed portion 60 is provided in one edge 60a of the pressure-sensitive adhesive tape package 10, in a portion 60b on the opposite side and in edges 60c and 60d provided between the these portions 60a and 60b. The heat-sealed portions 60a, 60c and 60d are linear, and are the same as those in the first embodiment. The remaining heat-sealed portion 60b is provided at a position away from the end; a portion 65 is not bonded such that the portion 65 can be held to open the package.

The heat-sealed portion 60b is a chevron or triangular sawtooth shape as illustrated. In the heat-sealed portion 60b with such a shape, when the portion 65 is held to pull the first release sheet 16 and the second release sheet 18 in the direction in which the first release sheet 16 and the second release sheet 18 are away from each other, the pulling force concentrates on one of peaks in the chevrons of the heat-sealed portion 60b, and breakage of the heat-sealed portion 60b starts from the peak. For example, in the case where the package is opened from the right upper end in FIG. 10, the force concentrates on the peak of the chevron shown by reference numeral 68. Particularly, because the peak of the chevron is a point in the shape shown in FIG. 10 and the pulling force concentrates on the one point even if the force is small, breakage starts easily. Once breakage starts in the heat-sealed portion 60b, the breakage propagates from the initial point of this breaking start point to other portion without applying an additional large pulling force to break the entire heat-sealed portion 60; thus, the pressure-sensitive adhesive tape package 10 reaches the state in FIG. 4(c).

The height of the chevron H and the pitch P in the heat-sealed portion 60b can be determined properly. In the case where P is larger than H, however, the angle of the peak of the chevron is large, and the effect of concentration of the force is impaired. Moreover, if P is small, the pulling force applied to the portion 65 is dispersed to 2 or more peaks of the chevrons, and a large force is required for opening. On the other hand, if H is small, the shape of the heat-sealed portion 60 a is close to that of the linear heat-sealed portion, and a large force is also required for opening in this case. In consideration of these points, it is suitable that H is around 10 mm, and P is approximately 10 to 20 mm.

FIG. 11(a) shows a modification of the heat-sealed portion 60 in FIG. 10, in which an inner edge of the heat-sealed portion 60b is linear. If one edge is linear as this, the feeling at the time of breaking the heat-sealed portion 60 is smooth.

Moreover, because breakage of the heat-sealed portion 60 is easy by concentrating the force on one point, only one projecting point 70 projecting toward the holding portion 65 is formed in the heat-sealed portion 60b as shown in FIG. 11(b). In the configuration of FIG. 11(b), portions other than the projecting point 70 of the heat-sealed portion 6a are gently sloped; this is for easily propagating breakage from the projecting point 70 to the other portions.

Further, means for bonding the first release sheet 16 and the second release sheet 18 is not limited to heat sealing, and a method using an adhesive or the like can be considered; at least one projecting point projecting outwardly is formed in the outer edge of the plane joint portion by an adhesive or the like, thereby to obtain the same easy openability as that in the heat-sealed portion 60a shown in FIGS. 10 and 11.

Figure 12:
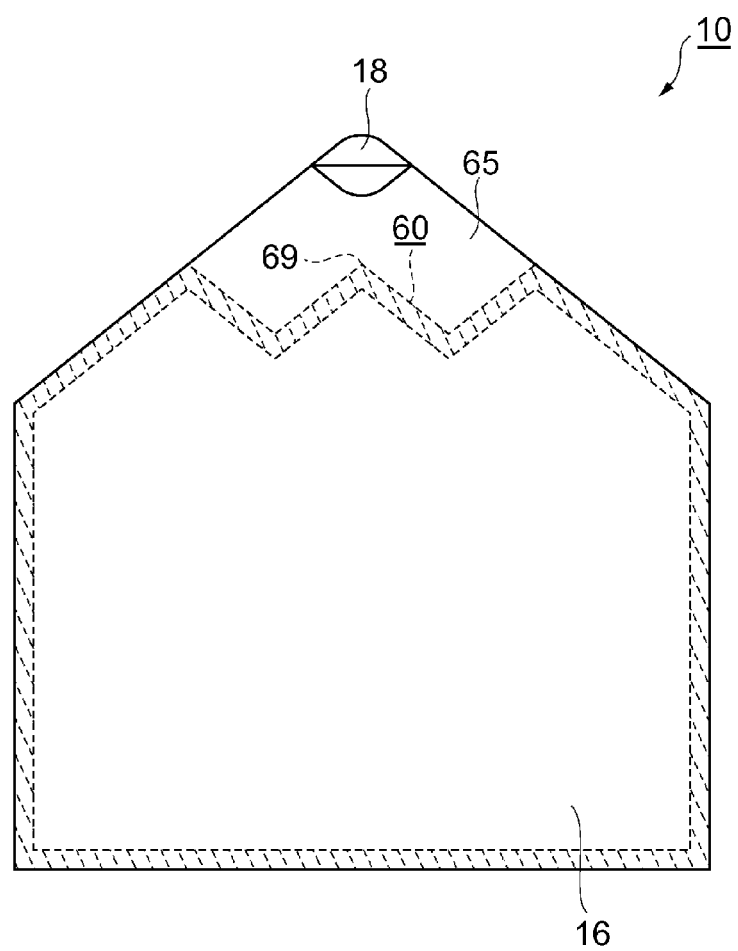
FIG. 12 is a schematic explanatory view showing further other modification of the second embodiment of the present invention.

Moreover, FIG. 12 shows an example in which a concept that the projecting points 68 and 70 described above are provided in the heat-sealed portion in the configuration in FIG. 8(b) is applied. In this configuration, the corner of the holding portion 65 faces an extending portion 69 of the heat-sealed portion 60. Because a user usually holds the corner to open the package 10, there are such features that a force easily acts on the extending portion 69 directly, and releasing is easy.

In the configurations in FIGS. 10, 11(a), 11(b), and 12, the configuration in FIG. 9(b) can also be applied. Namely, not shown, in the configuration in FIG. 10, for example, the one portion 65 of the first release sheet 16 and the second release sheet 18 can be longer than the other portion 65; in that case, the portion 65 can be held very easily, and it is effective for the user.

As above, the suitable first and second embodiments according to the present invention have been described in detail, but the present invention will not be limited to the embodiments above.

For example, while the case where the first release sheet, the second release sheet and the adhesive tape are approximately rectangular has been described in the description above, these may be any shape of various plane figures such as a square, a circle, an ellipse, and an oval figure.

Moreover, the production method according to the present invention is also not particularly limited, and production is enabled usually through a step of producing an adhesive tape, a step of bonding the first release sheet to the adhesive tape, and a step of superimposing the first release sheet and the second release sheet.

Moreover, in the embodiment above, it is configured such that the entire second release sheet is removed from the first release sheet and the adhesive tape (see FIG. 4(c)); alternatively, one side of the second release sheet may be securely bonded to one side of the first release sheet on the same side of the one side of the second release sheet, namely, the sides of the release sheets above are closed such that the second release sheet cannot be separated from the first release sheet. In such a configuration, because the second release sheet is not separated from the first release sheet, not only the end of the first release sheet but also the entire second release sheet can be held by hand at the time of applying the adhesive tape; thus, application is much easier.

Further, the bending line of the adhesive tape 14 does not need to be parallel to the sides of the release sheets 16 and 18.

Figure 13:
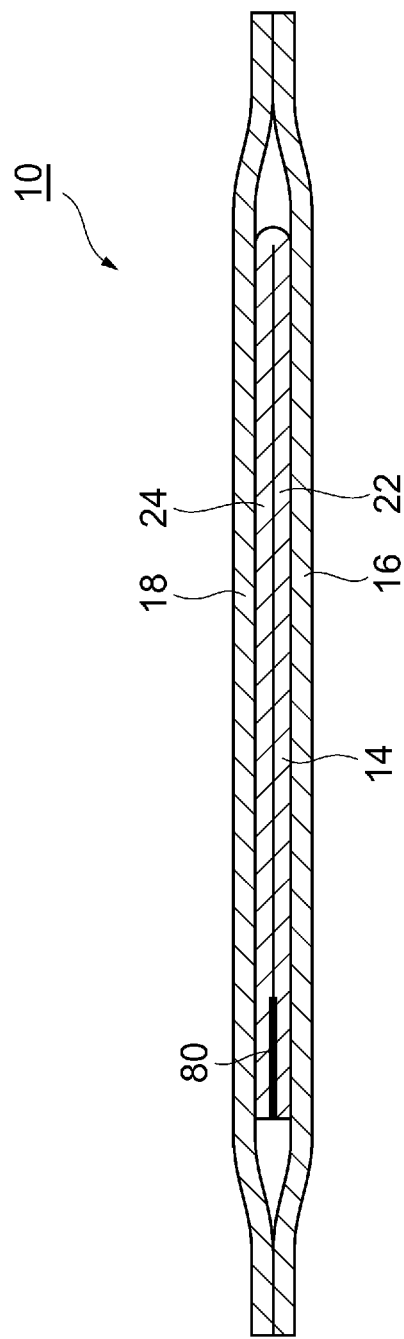
FIG. 13 is a sectional view showing other embodiment of the pressure-sensitive adhesive tape package according to the present invention.

FIG. 13 shows further other embodiment of the present invention, in which the area of the first portion 22 of the adhesive tape 14 is made substantially the same as that of the second portion 24; in other words, the first portion 22 and the second portion 24 are substantially in the same shape. In this case, the temporary attaching means 26 is not provided in the first release sheet 16, but needs to be provided between the first portion 22 and second portion 24 of the adhesive tape 14. This temporary attaching means 80 may be a pseudoadhesive or a hot-melt adhesive similarly to the embodiments above; alternatively, if the support 20 of the adhesive tape 14 is composed of a non-woven fabric, a method for entangling fibers can be used.

EXAMPLES

As an adhesive agent, 20 parts of a styrene-isoprene-styrene block copolymer, 20 parts of polyisobutylene, 45 parts of liquid paraffin, and 15 parts of hydrogenated rosin glycerol ester were mixed; the mixture was extended onto a polyethylene terephthalate woven fabric to obtain an adhesive tape. The adhesive tape was bent such that the adhesive agent might face outward and one end of the adhesive tape might be projected from the other end thereof A laminate film of polyethylene terephthalate, aluminum, and polyethylene (thickness of 80 μm) was cut such that the area thereof might be larger than that of the adhesive tape, and two laminate films were prepared as the release sheet. Then, the entire one surface of one of the release sheets was subjected to a silicone treatment as a means for reducing an adhesive force. Next, an adhesive agent as a temporary attaching means was applied to part of a portion of the other release sheet in which the extending portion of the adhesive tape was placed; subsequently, the adhesive tape was placed on the other release sheet, and the one release sheet was superimposed thereon. Subsequently, the edges of the two release sheets were heat-sealed such that the adhesive tape might be enclosed. Thereby, a pressure-sensitive adhesive tape package in the form shown in FIGS. 1(c) and 4(a) was obtained.

In the case where such a pressure-sensitive adhesive tape package was opened, as in FIG. 4(c), the bent adhesive tape was left on the release sheets. Subsequently, application to the skin was performed according to the procedure shown in FIGS. 5 to 7; the adhesive tape was easily applied to the skin securely and smoothly and it did not wrinkle.

According to the procedure of the Example above, the forming conditions on the heat sheet portion were changed to produce a plurality of pressure-sensitive adhesive tape packages with a shape shown in FIG. 10; the force needed for opening the heat-sealed portion (portion shown by reference numeral 60 a in FIG. 10) was measured by an opening force test, and performance of each package was evaluated by a function test.

In the opening force test, a tensile test Autograph AGS-1 kg NG (made by SHIMADZU Corporation) was used. Then, the opening ends of the package (upper portions of the holding portions 65 of the first release sheet 16 and the second release sheet 18 in FIG. 10) each were set on a holding jig, and a force per 25 mm width needed for opening the heat-sealed portion (portion shown by reference numeral 60b in FIG. 10) when the opening ends were pulled at an opening rate of 300 mm/min in opposite directions (when the so-called T-shaped opening was performed) was measured. The measurement results are as shown in the table below.

TABLE 1

|  | Force needed for opening (N/25 mm) | Result of function test (performance of package) |
| --- | --- | --- |
| Sample 1 | 15 | X |
| Sample 2 | 10 | ○ |
| Sample 3 | 5 | ◎ |
| Sample 4 | 1 | ◎ |
| Sample 5 | 0.5 | ○ |
| Sample 6 | 0.1 | X |

◎ Excellent (sealing performance is good and openability is high)
○ Good (sealing performance is good, or openability is high)
X Difficult to open, or sealing performance is bad From the table above, it turns out that the result of the function test is "good" when the force needed for opening the package is in the range of 0.5 to 10 N/25 mm, and the result of the function test is "excellent" particularly when the force is in the range of 1 to 5 N/25 mm From the results, it is desirable that the forming conditions of the heat-sealed portion are determined such that the force needed for opening the package may be in the range of 0.5 to 10 N/25 mm, and more preferably in the range of 1 to 5 N/25 mm Thereby, the pressure-sensitive adhesive tape package that is easy to open even for the elderly people and patients with physical weakness and whose sealing performance is good can be obtained.

REFERENCE SIGNS LIST

10 . . . pressure-sensitive adhesive tape package, 12 . . . adhesive agent layer, 14 . . . adhesive tape, 16 . . . first release sheet, 18 . . . second release sheet, 20 . . . support, 22 . . . first portion of adhesive tape, 24 . . . second portion of adhesive tape, 26 . . . temporary attaching means, 28 . . . silicone-treated surface (means for reducing an adhesive force), 30, 40 . . . non-bonded portion, 50 . . . notch, 60 . . . heat-sealed portion.

The invention claimed is:

1. A pressure-sensitive adhesive tape package that accommodates an adhesive tape having a support and an adhesive agent layer provided on one surface of the support,
    the adhesive tape being bent into a first portion and a second portion such that the adhesive agent layer faces outward,
    the pressure-sensitive adhesive tape package comprising a first release sheet releasably attached to the adhesive agent layer of the first portion of the adhesive tape, and a second release sheet releasably attached to the adhesive agent layer of the second portion of the adhesive tape to seal the adhesive tape with the first release sheet between the first and second release sheets,
wherein
    the first portion of the adhesive tape is substantially in the same shape as that of the second portion of the adhesive tape, and
    a temporary attachment is provided between the first portion of the adhesive tape and the second portion of the adhesive tape.

2. The pressure-sensitive adhesive tape package according to claim 1, wherein
    the first release sheet and the second release sheet are superimposed, and
    a portion surrounding the adhesive tape in which the first release sheet and the second release sheet are superimposed is sealed.

3. The pressure-sensitive adhesive tape package according to claim 1, wherein at least one projecting point projecting outward is formed in an outer edge of a face-to-face joint portion joining the first release sheet to second release sheet in a face-to-face relationship to seal therebetween.

4. The pressure-sensitive adhesive tape package according to claim 1, wherein a treated surface for reducing an adhesive force between the adhesive agent layer of the second portion of the adhesive tape and the second release sheet is provided on at least a part of the second release sheet.

5. The pressure-sensitive adhesive tape package according to claim 4, wherein the treated surface for reducing an adhesive force is a silicone-treated surface provided on at least a part of a portion of the second release sheet that is attached to the adhesive agent layer of the second portion of the adhesive tape.

6. The pressure-sensitive adhesive tape package according to claim 4, wherein the treated surface for reducing an adhesive force is an embossed surface and/or sanded surface provided on at least a part of the portion of the second release sheet that is attached to the adhesive agent layer of the second portion of the adhesive tape.

7. A pressure-sensitive adhesive tape package that accommodates an adhesive tape having a support and an adhesive agent layer provided on one surface of the support,
the adhesive tape being bent into a first portion and a second portion such that the adhesive agent layer faces outward,
the pressure-sensitive adhesive tape package comprising a first release sheet releasably attached to the adhesive agent layer of the first portion of the adhesive tape, and a second release sheet releasably attached to the adhesive agent layer of the second portion of the adhesive tape to seal the adhesive tape with the first release sheet between the first and second release sheets, wherein
the second portion of the adhesive tape is larger than the first portion of the adhesive tape, and the second portion has an extending portion that extends from the first portion, and
a temporary attachment is provided in at least a part of a portion facing the extending portion in part of the first release sheet.

8. The pressure-sensitive adhesive tape package according to claim 7, wherein an adhesive force of the support of the adhesive tape to the first release sheet through the temporary attachment is larger than an adhesive force of the adhesive agent layer to the second release sheet.

9. The pressure-sensitive adhesive tape package according to claim 1, wherein an adhesive force of the temporary attachment is larger than the adhesive force of the adhesive agent layer to the release sheet.

10. The pressure-sensitive adhesive tape package according to claim 7, wherein the temporary attachment has adhesiveness to the support of the adhesive tape.

11. The pressure-sensitive adhesive tape package according to claim 1, wherein the adhesive tape is used for medical care and applied to a skin or a mucous membrane.

12. The pressure-sensitive adhesive tape package according to claim 1, wherein after the second release sheet is removed, the adhesive agent layer of the second portion of the adhesive tape is exposed; and the pressure-sensitive adhesive tape can be applied by placing the exposed adhesive agent layer on or in the vicinity of a portion for application and then pulling the first release sheet in a direction in which the adhesive tape is released from the first release sheet while the first release sheet is held.

13. The pressure-sensitive adhesive tape package according to claim 1, wherein the temporary attachment is selected from the group consisting of a double-sided adhesive tape, an adhesive agent, an adhesive, pseudoadhesion, welding, thermal bonding, hard pressing, pressing, and a hot-melt adhesive.

14. The pressure-sensitive adhesive tape package according to claim 7, wherein the temporary attachment is selected from the group consisting of a double-sided adhesive tape, an adhesive agent, an adhesive, pseudoadhesion, welding, thermal bonding, hard pressing, pressing, and a hot-melt adhesive.

* * * * *